United States Patent [19]
van Damme

[11] Patent Number: 4,914,958
[45] Date of Patent: Apr. 10, 1990

[54] APPARATUS FOR INVESTIGATING THE BEHAVIOR OF CONTRAFORM CONTACTS

[75] Inventor: Eric van Damme, Braine l'Alleud, Belgium

[73] Assignee: Optimol Instruments GmbH, Munich, Fed. Rep. of Germany

[21] Appl. No.: 12,447

[22] Filed: Feb. 9, 1987

[30] Foreign Application Priority Data

Feb. 14, 1986 [DE] Fed. Rep. of Germany ....... 3604653

[51] Int. Cl.$^4$ ..................... G01M 13/00; G01N 3/56
[52] U.S. Cl. ......................................... 73/866.4; 73/7
[58] Field of Search ................... 73/865.9, 866.4, 804, 73/7

[56] References Cited

U.S. PATENT DOCUMENTS

| | | | |
|---|---|---|---|
| 4,268,257 | 5/1981 | Villar | 73/866.4 X |
| 4,432,223 | 2/1984 | Paquette et al. | 73/866.4 X |
| 4,532,802 | 8/1985 | Yeack-Scranton et al. | 73/866.4 |

FOREIGN PATENT DOCUMENTS

| | | | |
|---|---|---|---|
| 3140661 | 2/1983 | Fed. Rep. of Germany. | |
| 379845 | 7/1973 | U.S.S.R. | 73/7 |
| 879393 | 11/1981 | U.S.S.R. | 73/7 |
| 978011 | 12/1982 | U.S.S.R. | 73/7 |
| 1241099 | 6/1986 | U.S.S.R. | 73/7 |
| 678456 | 9/1952 | United Kingdom. | |

OTHER PUBLICATIONS

"Low-Temperature Wear-Test System"; *Ind. Lab.* (USA), vol. 44, No. 2, (Feb. 1978), (pub. Aug. 1978), pp. 284–286; E. A. Pamfilov et al.; in 73/7.

"Method of Testing Materials for Impact-Abrasive Wear"; *Ind. Lab.* (USA), vol. 46, No. 8, (Aug. 1980), (pub. Feb. 1981), pp. 847–850; G. M. Sorokin et al.; in 73/7.

"Method of Studying Abrasive Wear Resistance in Steels"; *Ind. Lab.* (USA); vol. 46, No. 12, (Dec. 1980), (pub. Jun. 1981), pp. 1296–1298; G. M. Sorokin et al.; 73/7.

*Primary Examiner*—Tom Noland
*Attorney, Agent, or Firm*—Toren, McGeady & Associates

[57] ABSTRACT

Testing apparatus for simulating the behavior of contact moving under normal force loading in machine components with at least two test objects and at least one first test object performs a rolling movement with or without a superimposed sliding movement on a second test object, in which at least the first test object can be driven by means of an eccentric arrangement, the latter including a first short crank receiving at a substantially constant speed about a first spindle, as well as a second short crank, which is articulated to the first crank on a second spindle at a distance from the first spindle, together with a third long crank, which is articulated to the second crank on a third spindle at a distance from the second spindle and is provided with a spatially fixed spindle at a distance from the third spindle and the fixed spindle is connected in non-rotary manner with spindles of the test object.

14 Claims, 6 Drawing Sheets

FIG. I

APPARATUS FOR INVESTIGATING THE BEHAVIOR OF CONTRAFORM CONTACTS

BACKGROUND OF THE INVENTION

The present invention relates to a testing apparatus for simulating the behavior of contacts in machine components moving under normal force action with at least two test objects including at least one first test objects which performs a rolling movement with or without a superimposed sliding movement on a second test object. For example, such apparatuses are required for simulating the engagement conditions of meshing gears.

The investigation of the permissible loading or stressing of meshing gears has long caused problems. These problems more particularly occur if, as is normally the case, the gears are lubricated. During tooth engagement, there is a change to the tangential velocities of the meshing tooth profile surfaces, the radii of curvature and, on passing from double to single engagement, the normal force. Moreover, due to their contraform design, tooth profiles are elastically deformed during loading and the lubricant is heated due to the frictional heat produced during engagement, so that the problem can only be theoretically solved in an approximate manner and with considerable programming and calculating expenditure on large computers.

Thus, considerable importance is still attached to the experimental investigation of tooth engagement. Due to the complicated engagement geometry and kinematics of the tooth system, attempts have been made to simulate tooth engagement in a so-called two disk or wheel test stand. However, such test stands suffer from the disadvantage that the change to the velocity for the engagement cannot be simulated. It is only possible to simulate individual operating points on the engagement path under stationary conditions and simulation thereof is not possible because of the non-stationary engagement conditions resulting from the change in the tangential velocity. The frequently used four disk or wheel test stands can also only be used for stationary operating conditions. Their main advantage compared with two disk test stands is that as a result of the symmetrical load application to the central disk, the latter can be mounted in an over high manner, which is more favorable from the measurement standpoint.

The experimental investigation of lubricated tooth systems causes particular difficulties. The most frequently encountered wear phenomena on lubricated tooth systems are scoring or fretting on the one hand and pitting on the other. Scoring mainly occurs on the tooth tips or crests, whereas pitting frequently occurs in the vicinity of the pitch point. Thus, scoring occurs in the area where the sliding velocity, i.e. the difference between the tangential velocities of the two profiles is high, whereas pitting occurs in the area where the sliding velocity is low or zero.

Theoretical research, confirmed by tests on disk test stands, reveals that the wear is essentially determined by the thickness of the lubricating film which builds up between the contact bodies. The known DOWSON formula for the approximate calculation of the lubricating film thickness states that the minimum lubricating film thickness in contact $h_{min}$ is proportional to the instantaneous tangential velocity of the tooth profiles $u_0^{0.7}$. $u_0$ being the arithmetic mean of the tangential velocities of the two profiles. Thus, during simulation, particular importance is attached to adapting the velocity conditions of the simulation apparatus to those of the tooth system.

Experimental research has also revealed that the results provided by disk test stands with respect to the formation of scoring and pitting can only be inadequately transferred to tooth systems, which can inter alia be attributed to differences in the velocity patterns. The variations are so great that tooth systems are used for investigating wear in the presently standardized wear tests, such as e.g. the FZG test according to DIN 51354. However, these tooth systems must be manufactured with high accuracy and ground and are consequently very expensive. Since, in addition, series results are necessary in order to obtain statistically informative test results, enormous cost are involved in such wear research.

German Specification No. 31 40 661 discloses an apparatus for simulating the stresses of gears rolling on one another with rotationally symmetrical disks, in which each disk is mounted in non-rotary manner on a swinging or rocking lever, the rotation axis of one lever being located on one side and the rotation axis of the other lever on the other side of the two disks, which are pressed together by bracing. A combined rolling/sliding movement is achieved by the movement of the swinging lever. This known apparatus has proved satisfactory, particularly when simulating the engagement conditions in slowly rotating, large gears. However, this apparatus is less suitable for simulating the engagement conditions of smaller, rapidly rotating tooth systems, because here the inert masses of the overall system become disadvantageously apparent.

SUMMARY OF THE INVENTION

The problem of the present invention is to provide a testing apparatus for simulating the behavior of contacts in machine components moving under normal force, permitting an optimum adaptation to the particular velocity relationships of the contacts to be simulated and which can be used at higher velocities or speeds.

In the case of an apparatus of the aforementioned type, this problem is inventively solved by at least the first test object being driven by means of an eccentric arrangement, the latter comprising a first short crank revolving at a substantially constant speed about a first spindle, as well as a second short crank, which is articulated to the first crank on a second spindle at a distance from the first spindle, together with a third long crank, which is articulated to the second crank on a third spindle at a distance from the second spindle and is provided with a spatially fixed spindle at a distance from said third spindle and the fixed spindle is connected in a non-rotary manner with spindles of the test object.

The inventive solution offers the possibility of being able to simulate within a wide range both rolling and sliding movements. The eccentric arrangement can in particular produce a rotary movement of the test object with periodic rotation direction reversal, so that in an advantageous manner the tangential velocities can e.g. be adapted to the velocity conditions in the tooth systems. A near reality and informative simulation of tooth engagement are possible through the attainable coincidence between the engagement relationships in the tooth system and the testing apparatus.

Unlike in continuously revolving test disks, such as are used in the case of two and four disk test stands, it is possible here to limit the contact of the two test objects to a particular circumferential region of the test objects. This has the advantage that a single test disk can be used for several tests, it merely being necessary to rotate on by a corresponding angle the test object, so that an unworn circumferential region comes into contact. It also offers the advantage that the necessary operations for the fatigue strength tests can be more rapidly achieved than in the case of conventional two disk machines, because here loading is only limited to a short region.

The periodic reciprocation possible with the inventive eccentric drive also offers measuring advantages. In the known two and four disk test stands, considerable apparatus expenditure is required for transmitting the measured signals, e.g. for a friction measurement or a lubricating film thickness measurement, from the rotary shaft to the measuring equipment. In addition, such rotation transmitters also have a certain influence on the measured signal, which is particularly disadvantageous in the very complicated capacitive lubricating film thickness measurement. The inventive solution offers the advantage here that there are no complete revolutions of the test object, so that the latter can be directly connected by cables to the measuring equipment. There is no need to use rotation transmitters for the contacting or non-contacting transmission of measured signals.

The eccentric drive which comprises three cranks can be adapted by matching the individual crank lengths to the particular simulation case. An example of the design of the eccentric drive for simulating a toothed gear is given in the specific description relative to the drawings. It is particularly advantageous that the length of the long crank can be freely selected within the kinematic and geometrical possibilities of the testing apparatus. This means that for adapting the testing apparatus to different simulation cases, e.g. to tooth systems with different gear tooth proportions, it is merely necessary to modify the length of the two short cranks. This can e.g. be brought about in that sets of different crank pairs are used, one crank pair comprising the first short crank and the second short crank, which in each case correspond to a given tooth system design. It is also possible according to a preferred embodiment to modify the position of the axes on the cranks, so that the crank length is adjustable. This has the advantage that the cranks can be rapidly adapted to different simulation cases.

The inertia forces of the crank gear normally cause no problems. According to a preferred embodiment, however, counterweights are provided on the cranks, in order to compensate the moment of inertia thereof in such a way that no free inertia forces result from the rotation of the cranks. This offers the advantage that the operation of the testing apparatus can take place without difficulty, even at high speeds.

According to a preferred embodiment, the testing apparatus has two test objects, which are in the form of test disks. This apparatus is particularly suitable for simulating toothed gears.

According to another preferred embodiment, the testing apparatus has three test objects, whose axes are either located within a straight line or whose axes form the angle points of an equilateral or scalene triangle. This embodiment has the advantage that two contacts can be investigated in one test run and e.g. different material combinations can be used. Thus, it is possible when arranging the axes of the test objects on a straight line to make the central test object from a given material and the two other test objects from, in each case, a different material. This makes it possible to investigate which material combination leads to wear occurring first.

According to a another embodiment, four test objects are used, a central test object being surrounded in a satellite-like manner by three symmetrically arranged test objects. This makes it possible to investigate several different contact conditions at once. It is particularly advantageous that only one of the test objects has to have a pressure device, because the contact pressure of the other contacts is obtained as a force of reaction. Apart from the variation of the material, it is also possible to compare in a single test variations of production, i.e. the combination of different roughnesses during grinding.

According to yet another preferred embodiment, there is only one test body driven by the eccentric arrangement and this is in contact with a second, not driven test object. With this arrangement two different test conditions are possible. Firstly, the second, undriven test object can be mounted in such a way that it follows the movement of the first eccentric-driven test object. This makes it possible to investigate the loading of the test object during rolling at different rolling speeds. Such a test arrangement is e.g. particularly suitable for investigating pitting. It is secondly possible to fix the second test object, so that it is e.g. possible to investigate the contact between a rotary cam and a ram with a fixed surface.

According to still another preferred embodiment, the test objects have a rotationally symmetrical construction. However, according to another preferred embodiment use is made of non-rotationally symmetrical test objects, in order to investigate special contact conditions. It must then either be insured that the sum of the contact spacings of the particular test objects remains constant, or there must be a compensation of the center distance change, e.g. through a corresponding pressing device.

The first short crank is conventionally driven at a constant velocity. According to a preferred embodiment the transfer of the driving torque to the first crank takes place non-positively, e.g. using a belt and chain drive, such as a belt drive, or by means of a friction drive.

According to another embodiment, the transfer of the driving torque to the fulcrum of the first crank takes place positively using a toothed gear of a toothed belt.

The transfer of the movement to a second test object can be performed in simple manner in that the driving shaft for driving the crank of the first test object is also used for driving the second test object. In this case there must be a corresponding transfer to the second test object by means of a suitable device, e.g. a cardan shaft.

According to a further preferred embodiment, the driving torque from a drive motor is directly distributed to the particular eccentric drives. This can e.g. take place by means of tooth systems, which are arranged in accordance with the test disks and which bring about a synchronous running of the driving shafts of the individual eccentric drives. However, it is also possible to provide a timing belt drive, which runs via the individual driving shafts and which consequently also brings about a synchronous driving of the different eccentrics.

According to another preferred embodiment, one test body is arranged in the other, so that a conform contact is obtained with, as a function of the diameter relationship, good or poor osculation. The first, outer test object is then constructed in such a way that it has a cylindrical depression, the inner wall of the cylinder serving as a contact surface with the second test object. The diameter of the second test object is smaller than that of the cylindrical depression and the second test object is arranged in such a way that it is in contact on said inner surface with the first test object. This e.g. makes it possible to simulate the movement relationships of inner tooth systems.

According to further preferred embodiment, the testing apparatus is provided with means making it possible to modify the loading during rotary movements of the test object. When simulating toothed gears the loading change can be such that loading is reduced to zero in the vicinity of the reversal points of the rotary movement, where the test object is briefly stationary, or during the return travel. In the case of a hydraulic loading device, this can be achieved in a simple manner by means of a corresponding pressure drop, which is brought about mechanically or electronically by a sensor or is periodically coupled to the rotary movement. This load change has the advantage that it is possible to simulate the intermittent loading conditions of the tooth system, resulting there from the discontinuously occurring tooth engagement.

Further advantages, features and possible uses of the present invention can be gathered from the following description relative to the drawings.

BRIEF DESCRIPTION OF THE DRAWINGS

FIG. 13, shows an arrangement having three test objects with their axes in one plane.

FIG. 14, shows an arrangement having three test objects with their axes forming the points of a triangle.

FIG. 15, shows an arrangement wherein the test objects are not rotationally symmetrical.

DETAILED DESCRIPTION OF THE PREFERRED EMBODIMENT

Figure 1:
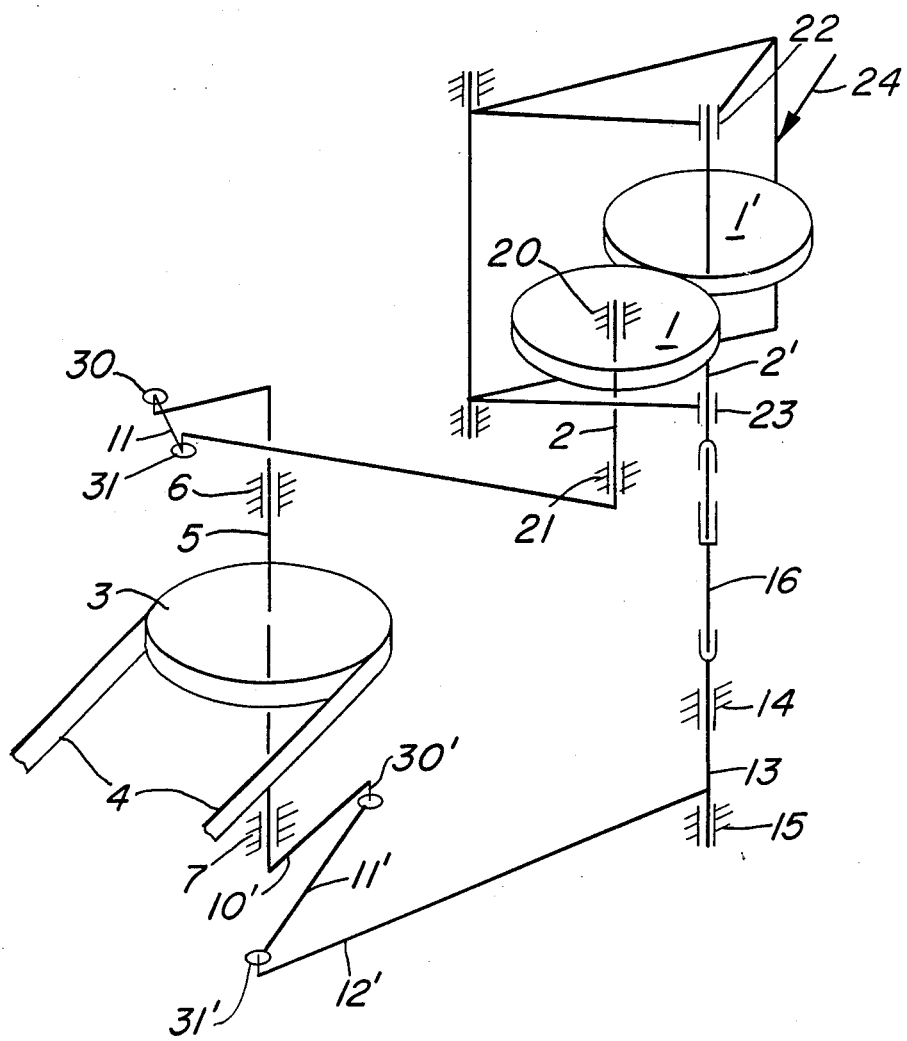
FIG. 1, a diagrammatic sketch making clear the function of the inventive testing apparatus.

FIG. 1 is a diagrammatic sketch of an embodiment of the inventive testing apparatus, which comprises the two test disks 1, 1', test disk 1 having a spatially fixed spindle 2 and test disk 1' a displaceable spindle 2'. In the represented embodiment, the testing apparatus is driven by means of a pulley 3 with a belt 4. This pulley can e.g. be a V-belt pulley and the belt 4 can be a V-belt, but it is also possible to use a flat plastic belt or a timing belt drive. The driving action can also be brought about by an electric motor with a through shaft, which has the advantage that any vibrations or oscillations caused by the belt drive are not transferred to the test objects. The pulley is connected to a shaft 5, which is mounted in two bearings 6, 7. At either end of the shaft is provided a short crank 10, 10' connected in non-rotary manner to shaft 5. A second short crank 11, 11' is articulated to said first short crank 10, 10' by means of a pin 30, 30'. Two long cranks 12, 12' are articulated in a rotary manner to the two short cranks by means of pins 31, 31'. The long crank 12 is connected in a non-rotary manner with spindle 2 of test object 1 and consequently transfers its reciprocating rotary movement directly to test object 1. The movement of long crank 12' is transferred by means of a length and angle-compensating cardan shaft 16 to test object 1', in order to compensate for the change in the angular position of test object 1' when applying the normal force and also manufacturing tolerances. Therefore, long crank 12' has a shaft 13 mounted in a rotary manner in two bearings 14, 15. Shaft 13 is connected to cardan shaft 16, which is in turn connected in a non-rotary manner to spindle 2' of the test object. Test object 1 is mounted in two spatially fixed bearings 20, 21, while the test object 1' has movable bearings 22, 23. These two bearings can be used for applying a normal force in the direction of arrow 24 to the test objects. The counterforce to said normal force is brought about by bearings 20, 21.

The apparatus functions in the following way. If pulley 3 is driven at a constant speed by belt 4, shaft 5 also rotates at a constant speed. Therefore the two short cranks 10, 10' also rotate at a constant speed about the spatially fixed shaft 5. Therefore spindles 30, 30' connecting the first short cranks 10, 10' with the second short cranks 11, 11' also rotate at constant speed. Spindles 31, 31' located between the second short cranks 11, 11' and long cranks 12, 12' can only perform a rotary movement about the spatially fixed spindle 2 or 13. Thus, the rotation of short cranks 10, 10' leads to a corresponding reciprocating movement of long cranks 12, 12' and therefore of the test objects.

The length of the two short cranks and the long crank must be adapted to the particular simulation case. In all cases, the length of the long crank 12, plus the length of the second short crank 11 must at least be as long as the spacing of spindles 2 and 5, plus the length of the short crank 10.

The adaptation of the crank length to the particular simulation case is subsequently explained in a theoretical manner and with the aid of a practical example.

Figure 2:
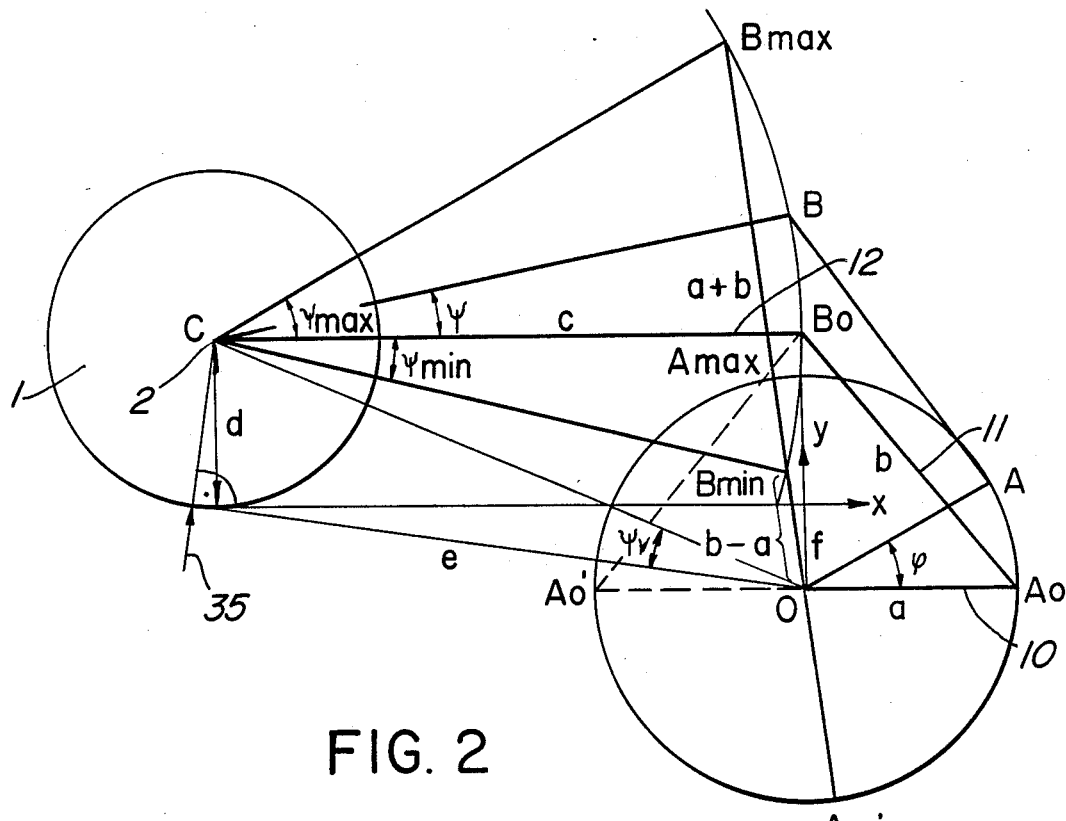
FIG. 2, the geometrical connections for the design of the testing apparatus.
Figure 3:
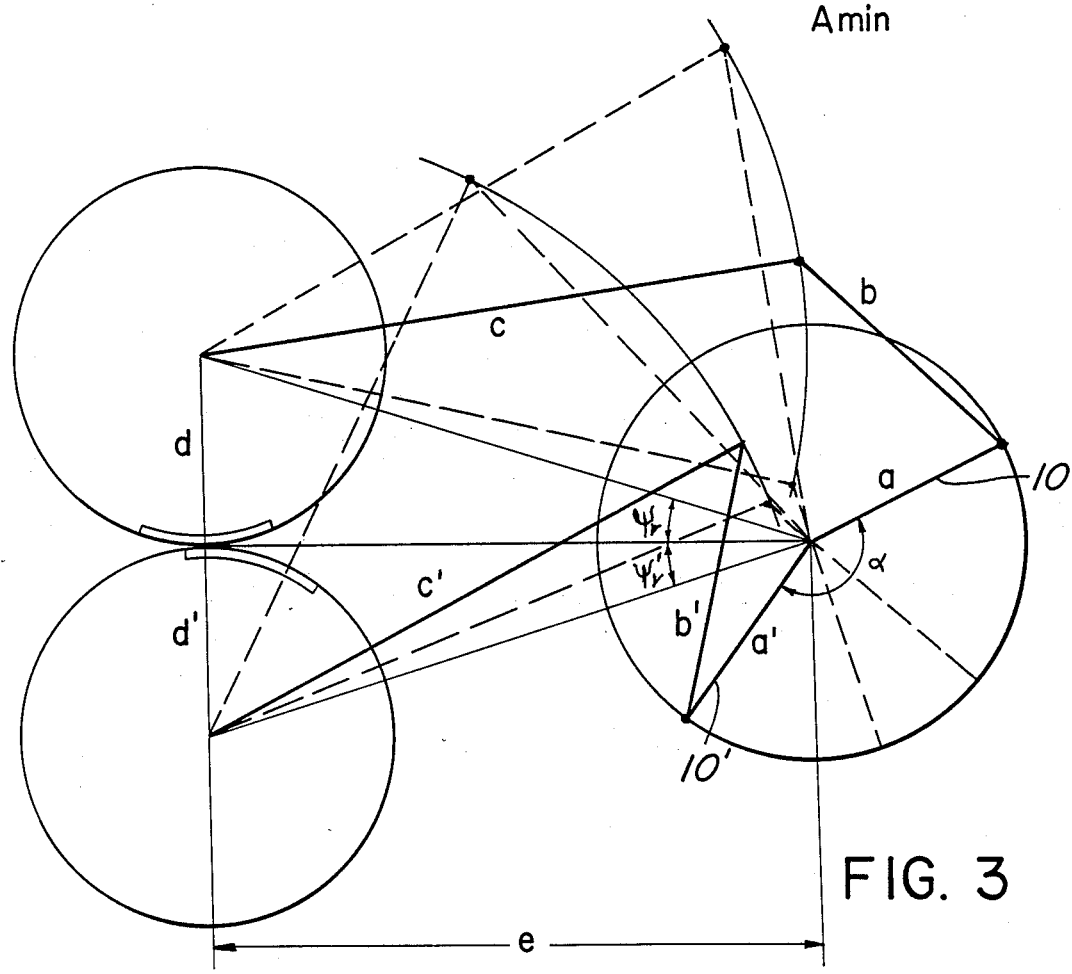
FIG. 3, another representation concerning the design of the test stand.

FIGS. 2 and 3 show the geometrical relationships required for the kinematic analysis of the inventive testing apparatus. FIG. 2 shows testing disk 1 with the geometrical center C and the diameter d. The rotation axis of the eccentric device, which in this embodiment coincides with shaft 5, is designated 0 and the contact point is marked with the arrow 35. The first short crank 10 has the length a, while the second short crank 11 has the length b. The long crank 12, which is connected in a non-rotary manner to spindle 2 of test object 1, has the length c. The important prerequisite for a successful simulation is that the velocity pattern of the tangential velocities of the tooth profiles is achieved to the greatest possible extent. Not only is importance attached to the adaptation of the cranks, but also a realistic pitch point must be found for the apparatus. It must be borne in mind that the pitch points do not automatically coincide in the reciprocating motions of the apparatus. This important condition for correct simulation must be fulfilled by the design. The position of the cranks in the pitch point is therefore designated by $A_O$ and $B_O$. The position of the cranks according to a random, other rotation angle $\phi$ is designated by A and B. The maximum deflection or displacement is represented by $A_{max}$ and $B_{max}$ and the minimum displacement or deflection by $B_{min}$. The associated angles on the test object are designated $\Psi_{min}$, $\Psi$ and $\Psi_{max}$. The distance between the transverse axis O of the crank system and contact point 35 of the test object is e.

Essentially the same geometrical conditions apply for the second test object and its position is designated by $A'_O$. $A_O$ and $A'_O$ must be symmetrical to $B_O$ and be located on a straight line through rotation axis O, so that by rotating crank a by $\phi=180°$, $A_O$ can be converted into $A'_O$ and then $B_O$ coincides for both cases. Crank 12 of length c and the distance $B_O$-O are perpendicular to one another.

The best coincidence between the velocity relationships between the toothed gear to be simulated and the testing apparatus is obtained if the radii of curvature in the pitch point of the gears to be simulated are chosen for the radii d and d' of the two test objects. One skilled in the art knows how to determine these radii of curvature and therefore there is no need to explain here.

Another condition for the simulation is that the length of the overrolled part of the test disks must be as long as the corresponding lengths of the tooth profiles. Thus, for both tooth profiles, it is firstly necessary to determine the length of the active involute, namely $S_{1ac}$, the length of the involute between the start of engagement and the pitch point of the pinion; $S_{1ec}$, the profile length between the pitch point and the end of engagement of the pinion; $S_{2ac}$, the length between the start of engagement and the pitch point on the rack and $S_{2ec}$ as the distance between the pitch point and the end of engagement on the rack. These lengths can be readily obtained from the geometry of the tooth system and can be determined by one skilled in the art on the basis of standard calculation specifications. From the involute length and the corresponding diameter of the test object 1, the following displacement or deflection angle for crank 12 can be obtained for the corresponding distances, $\Psi_{max}$ representing the maximum deflection and $\Psi_{min}$ the minimum deflection:

$$\psi_{max} = \frac{S_{1AC}}{d}$$

$$\psi_{min} = \frac{S_{1EC}}{d}$$

For the second test object 1' with the diameter a' the following values are obtained:

$$\psi_{max'} = \frac{S_{2EC}}{d'}$$

$$\psi_{min'} = \frac{S_{2AC}}{d'}$$

On the basis of these geometrical relationships for the deflection or displacement of crank 12, it is possible to calculate the unsupported or lever lengths a, b and c or a', b' and c' of the testing apparatus. A coordinate system X, Y, as shown in FIG. 2 is used for calculation purposes. The position of this coordinate system is determined by the position of the cranks in the pitch point. The X-axis is at distance d parallel to crank 12 in the pitch point position, while the Y-axis is perpendicular to the X-axis and runs through the intersection between crank 11 and crank 12. The geometrical links lead to the following equations:

$$(X_{Bmin} + c)^2 + (Y_{Bmin} - d)^2 = c^2$$

$$X_{Bmin}^2 + \left(Y_{Bmin} - d + \sqrt{b^2 - a^2}\right)^2 = (b - a)^2$$

$$\sin \psi_{min} = \frac{(d - Y_{Bmin})}{c}$$

$$(X_{Bmax} + c)^2 + (Y_{Bmax} - d)^2 = c^2$$

$$X_{Bmax}^2 + \left(Y_{Bmax} - d + \sqrt{b^2 - a^2}\right)^2 = (a + b)^2$$

$$\sin \psi_{max} = \frac{Y_{Bmax} - d}{c}$$

These six equations contain the seven unknown quantities $X_{Bmin}$, $Y_{Bmin}$, $X_{Bmax}$, $Y_{Bmax}$ and the unsupported length a, b and c. The equation system can be solved in an iterative manner and the crank length c can be fixed beforehand. The iterative solution of such an equation is known and appropriately use is made of electronic calculating aids, such as e.g. a microcomputer.

The same equations apply to the calculation of the crank lengths a', b'and c' for the drive of the second test object 1'. Crank length c' is firstly given with a random value and must be adapted after carrying out the iterative calculation. The construction of the testing apparatus according to FIG. 5 leads to the condition that the distance between the rotation axis of the drive and the contact point of the two test discs for both eccentric drives must be the same. Therefore, the crank lengths for the drive of the second test object 1' must be chosen in such a way that the distance e of the drive of the first test object is the same as the distance e' of the second test object and the following relationships apply:

$$e^2 = c^2 + b^2 - a^2 - d^2$$

$$e'^2 = c'^2 + b'^2 - a'^2 - d'^2.$$

The crank lengths for the drive of the second test object are now linearly increased or decreased in such a way that ratio of the distance $e/e' = 1$.

Thus, the crank lengths and center-to-center distances necessary for the simulation are determined. It is still necessary to establish the magnitude of the angle $\alpha$ (cf FIG. 3) between the two cranks 10, 10'. This angle must be such that the calculated pitch points for the two test objects coincide. Angle $\alpha$ is obtained from the geometry of the testing apparatus by the relationship:

$$\alpha = 180° - (\psi_r + \psi_{r'})$$

in which $\omega_r$ is identical $$\psi_r = \arctan\left(\frac{1}{\sqrt{\frac{c^2 + b^2 - a^2}{d^2} - 1}}\right)$$

and

-continued $$\psi_{r'} = \arctan\left(\frac{1}{\sqrt{\frac{c'^2 + b'^2 - a'^2}{d'^2} - 1}}\right)$$

The calculation of the geometry of the testing apparatus is concluded on determining angle $\alpha$.

As an example, the results of the calculation for the following case are given. It was necessary to simulate a tooth system with a modulus of 10 mm and with 12 teeth on the rack and pinion. The center-to-center distance was 120 mm and the profile displacement 0. The engagement angle on the rolling circle was 20° and the outside diameters of the gears were 139.5 mm, giving the following values for the testing apparatus. (in this example the lengths of the cranks for both drives and the diameters of the test disks are identical.)

| Test disk diameter | $d = 20.521$ mm |
| --- | --- |
| Maximum deflection of crank 12 | $\psi_{max} = 31.281°$ |
| Minimum deflection of crank 12 | $\psi_{min} = 10.427°$ |
| Length of first short crank 10 | $a = 29.547$ mm |
| Length of second short crank 11 | $b = 37.120$ mm |
| Length of long crank 12 | $c = 83$ mm |
| Distance between test object axis and drive axis | $e = 83.503$ mm |
| Angle between cranks 10 and 10' | $\alpha = 152.386°$ |

Figure 4:
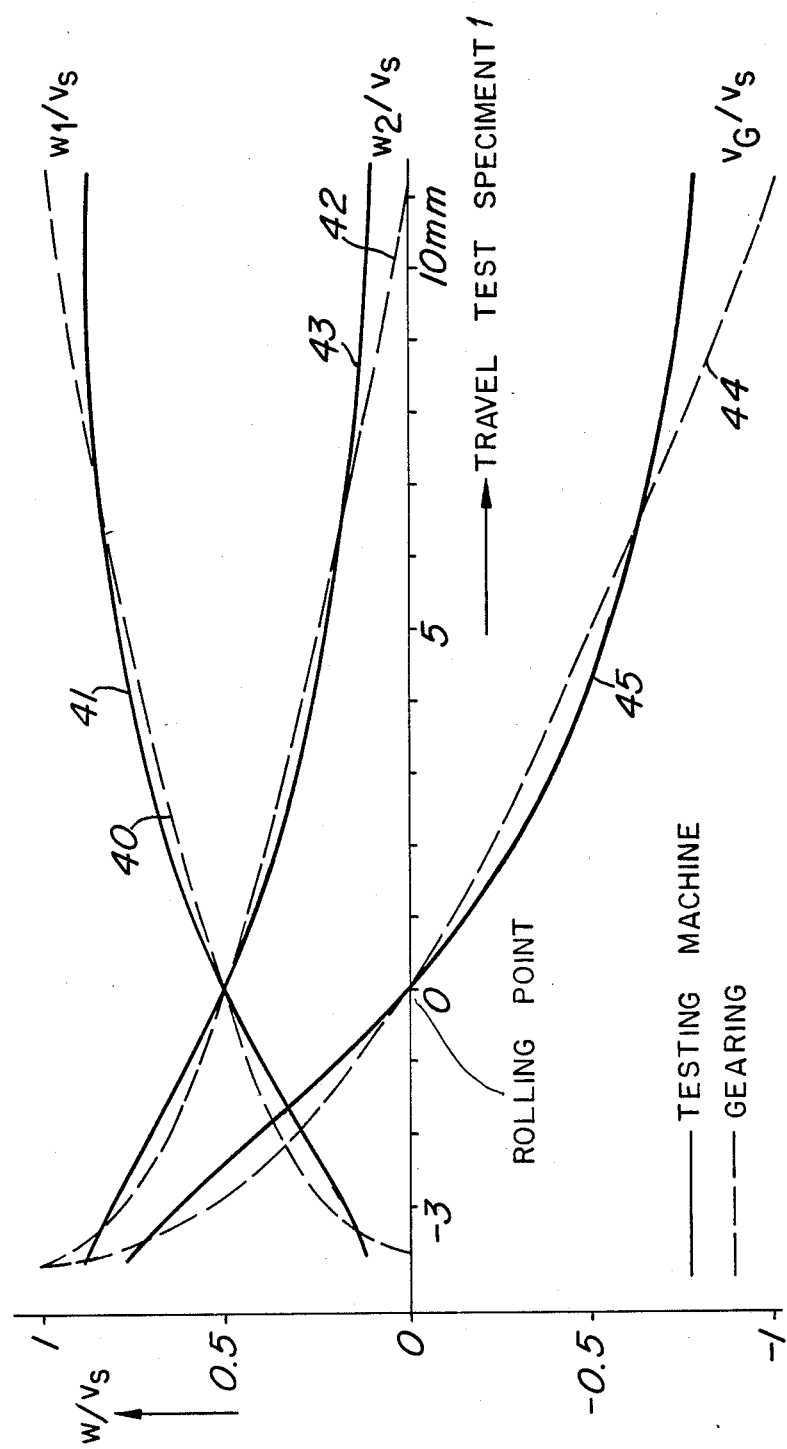
FIG. 4, the velocity conditions in a comparison between the testing apparatus and a toothed gear.

The velocity relationships obtained with this design are given in FIG. 4. The broken line indicates the pattern of the velocity in the toothed gear, while the continuous line represents the velocity pattern in the testing apparatus. On the ordinate axis is plotted the ratio of the tangential velocity w to the sum velocity of the two engaging objects. The sum velocity $v_S$, which is also called the hydrodynamically active velocity, is the essential characteristic value for the formation of a lubricating film, because only in the case of an adequately high sum velocity can oil be fed into the lubricating gap. On the abscissa is plotted the path covered on the test object or the involute of the test system. The length is measured from the pitch point.

Curve 40 shows the velocity pattern of pinion $w_1$ relative to the sum velocity $v_S$. The adjacent curve 41 shows the same curve for the test object 1 of the testing apparatus. Curve 42 represents the velocity change of the rack of the toothed gear, while curve 43 corresponds to curve 41 for test object 1'. Finally, curve 44 represents the pattern of the sliding velocity in the tooth system, once again related to the sum velocity $V_S$. The sliding velocity is responsible for the heating of the toothed gear and therefore in particular for the occurrence of scoring. Curve 45 shows the corresponding sliding velocity pattern for the testing apparatus. It is possible to see that all the velocity values of the toothed gear and the testing apparatus essential for lubricating film formation and wear coincide extremely well. Thus, the problem of bringing about a near reality simulation of the processes in the toothed gear is solved.

An embodiment of the inventive testing apparatus is shown in FIGS. 5 to 11 and for simplification purposes the same references are used as in the description of FIG. 1.

Figure 5:
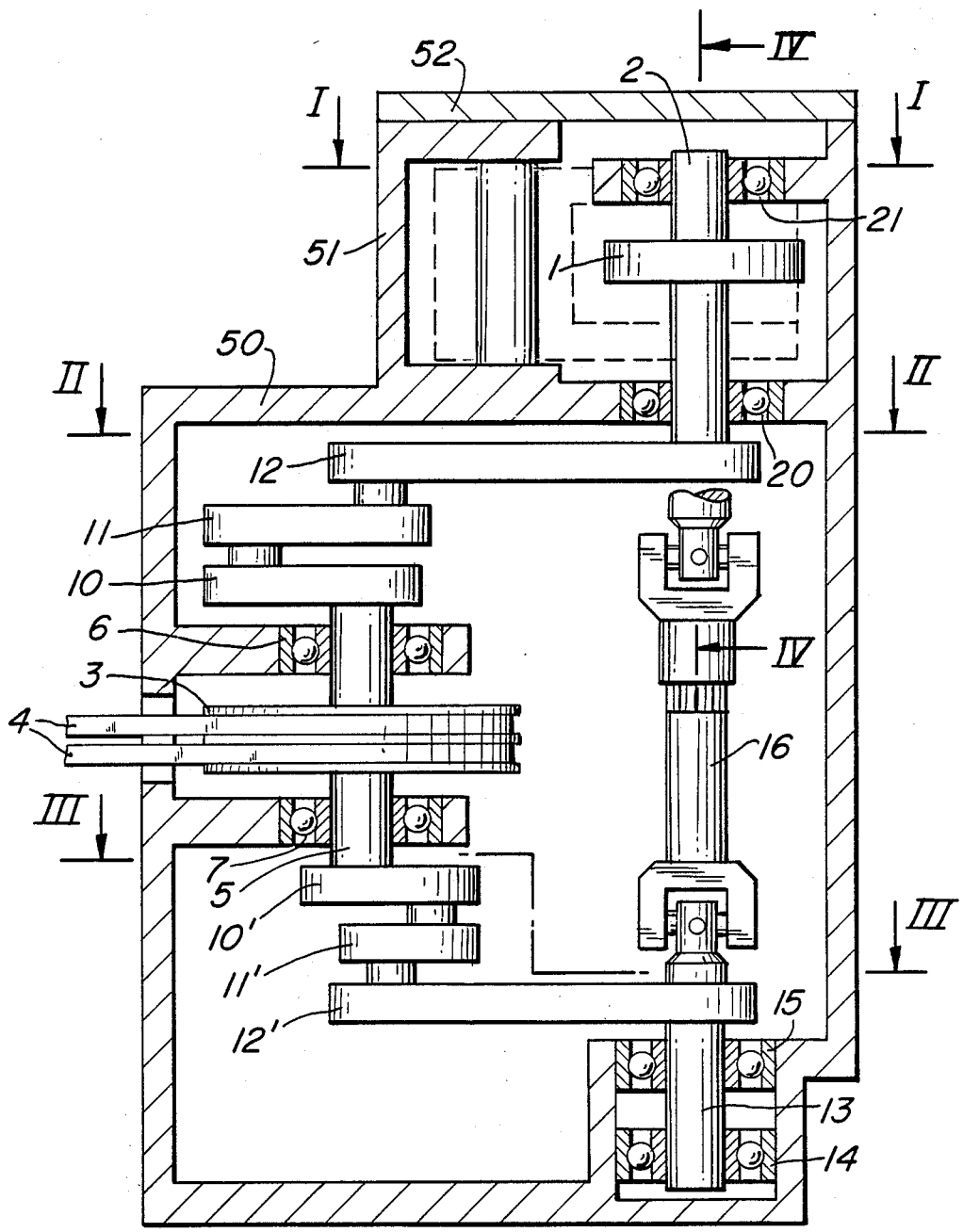
FIG. 5, a diagrammatic view of the construction of the testing apparatus in a part section side view.

FIG. 5 is a side view of the testing apparatus. Test disk 1 is located on a shaft 2, which is once again mounted in two antifriction bearings 20, 21. It is pointed out that, as a function of the operating conditions, these and other antifriction bearings can be replaced by hydrodynamically or hydrostatically acting plain bearings.

Shaft 2 is connected in non-rotary manner with long crank 12, which is in turn connected in rotary manner to crank 11. The individual parts of the rotary connection between the individual cranks need not be shown, because they are well known to the expert in the field. The second short crank 11 is connected in a rotary manner to the first short crank 10, which is located in a non-rotary manner on shaft 5. Shaft 5 is mounted in antifriction bearings 6, 7 and carries in its center a double pulley 3 with two V-belts 4. The latter can be replaced by a flat belt drive, e.g. using a plastic belt or a timing belt drive. In a different spatial configuration of shaft 5, it is also possible to fit the electrical driving means directly thereon. However, in this case it must be borne in mind that the antifriction bearings can introduce oil into this part of the casing. On its lower side, shaft 5 is connected in a non-rotary manner to the first short crank 10', which is connected in a rotary manner to the second short crank 11', which is in turn connected to long crank 12'. Long crank 12' is connected in a non-rotary manner to a shaft 13, which is mounted in an overhung manner in antifriction bearings 14, 15. A cardan shaft 16, which can compensate both angular and length changes is connected in a non-rotary manner to shaft 13. Cardan shaft 16 is required, because the test object 1', which cannot be seen in this position, must be pressable onto test object 1 without any counteraction of the drive.

A counterweight 5a is provided on the short crank 10' to balance the crank. The use of such counterweights is well known in internal combustion engines.

The complete testing apparatus is housed in a casing having a lower casing part 50 and an upper casing part 51. The casing is closed by a cover 52. The individual parts of the casing result from constructional requirements and need not be explained.

Figure 6:
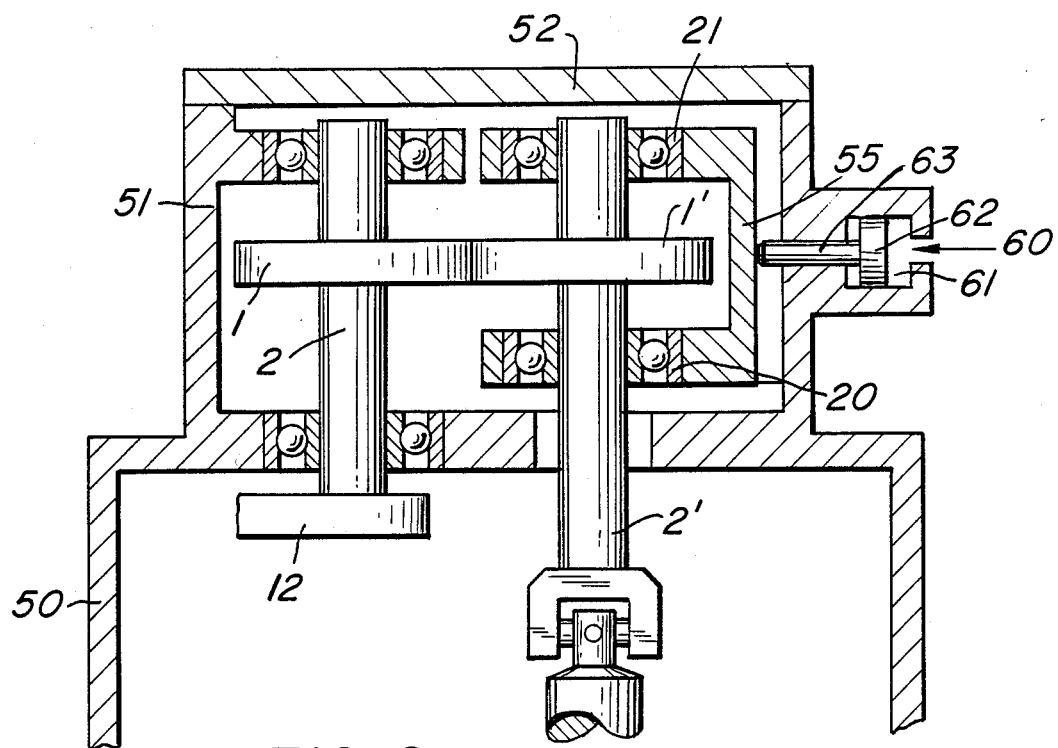
FIG. 6, a section along line IV—IV in FIG. 5.
Figure 7:
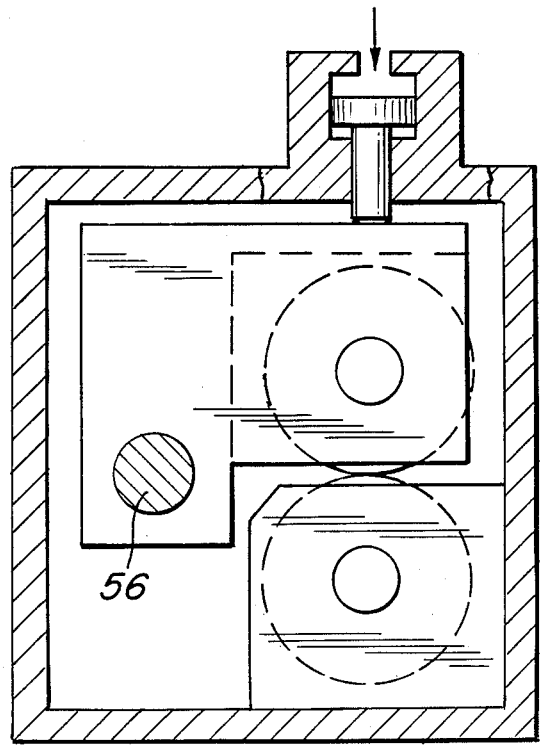
FIG. 7, a section along line I—I in FIG. 5.
Figure 8:
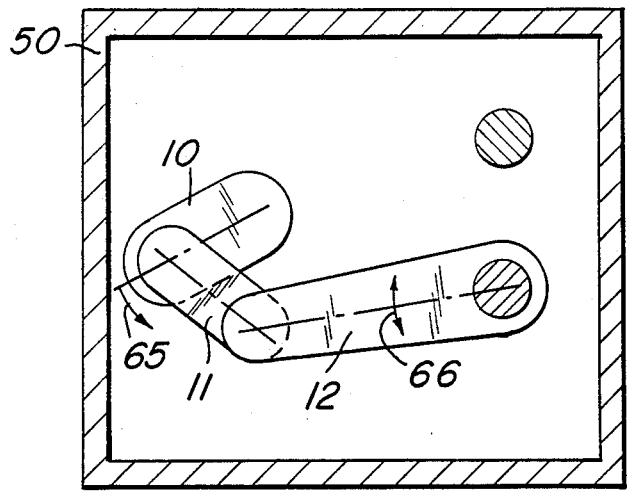
FIG. 8, a section along line II—II in FIG. 5.
Figure 9:
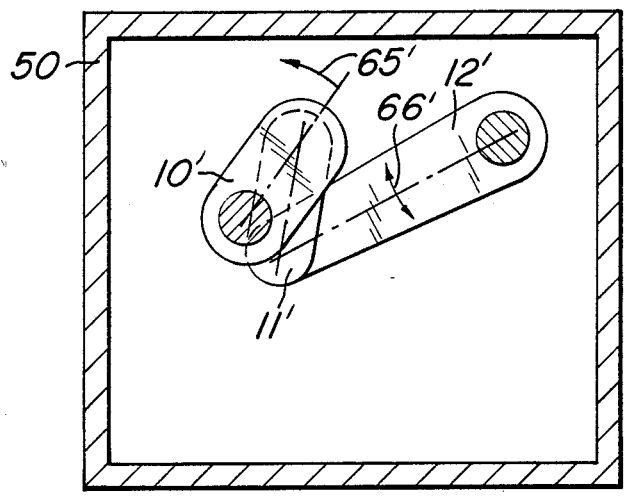
FIG. 9, a section along line III—III in FIG. 5.
Figure 11:
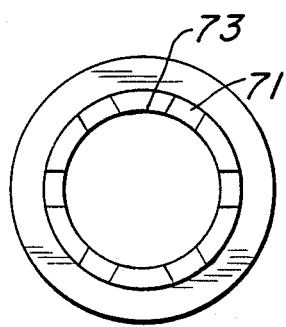
FIG. 11, the construction of the test disk.
Figure 12:
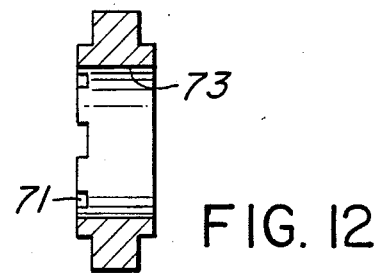
FIG. 12, a section through the test disk.

FIG. 6 is a side view rotated by 90° compared with FIG. 5. It is possible to see the interaction of test objects 1, 1' and the mounting thereof in the casing. It is also possible to see the function of the pressing apparatus for pressing the test disk 1' on test disk 1. Test disk 1' with its shaft 2' is mounted in antifriction bearings 21, 20, which are received by a rotary frame 55. As can be seen in the sectional view of FIG. 7, this frame is articulated in a rotary manner about shaft 56. Load application takes place in that pressure oil is supplied to the pressure chamber 61 of the loading device 60. This oil acts on plunger 62 which, by means of the pressure plate 63, transfers the force produced to the frame 55 of test disk 1'. The application of the load via this hydraulic system has the particular advantage that the particular loading level can be simply read off by means of a pressure gauge. The driving force is obtained in that the pressure is multiplied by the surface of plunger 62. FIGS. 8 and 9 show two further section views through the testing apparatus. FIG. 8 is a section along line II—II in FIG. 5 with a plan view of the eccentric arrangement for driving the test disk 1 through the rotation of short crank 10 in the direction of arrow 65. On crank 12, via crank 11 there is a reciprocating movement in the direction of arrow 66. This takes place in the same way for the drive for test disk 1', which is shown in FIG. 9. The rotation of short crank 10' in the direction of arrow 65' lead to a reciprocating movement of long crank 12' in the direction of arrow 66'. The axes of the individual cranks are represented in simplified form by crosses or the intersections of the dotted symmetry lines of the different cranks. A counterweight 66d is provided on the crank 12 to counterbalance the weight of the cranks.

Figure 10:
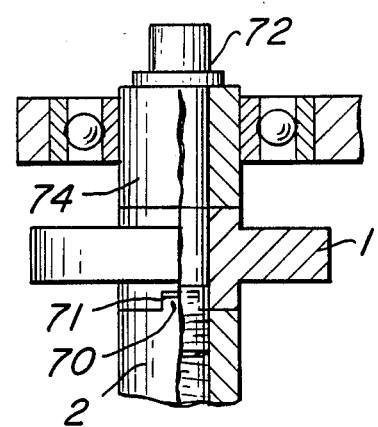
FIG. 10, the fixing of the test disks in part section.

Another important function of the invention is to provide changing means for the test disks, which on the one hand permits a rapid changing of the disks, but on the other reliably absorbs the reciprocating movements of the eccentric drive and can pass them to the test disks. The invention proposes fixing the test disks with a concentric tight-fit screw, the rotation transfer from shaft 2, 2' to the tests disks taking place by means of radial grooves. The details of this connection are shown in FIG. 10. Shaft 2 or 2' has projections 7, which are equidistantly distributed about the shaft. As can in particular be gathered from FIG. 11, test disk 1 has corresponding radially grooves 71, which are radially distributed over the entire circumference. The actual fixing takes place by means of the tight-fit screw 73, which passes through a corresponding bore in test disk 73. A correspondingly worked intermediate part 74 forms the pin for the antifriction bearing 20.

The represented embodiment was developed in order to permit the simulation of toothed gears. However, it is pointed out that in the case of a different configuration of the same eccentric arrangement it is also possible to apply combined rolling—sliding contacts, such as occur in various other technical fields, e.g. when simulating cam—ram pairs or in the case of antifriction bearings.

An arrangement utilizing three test objects is illustrated in FIG. 13. In this arrangement, three test objects 80, 81, 82 are aligned so that their axes are in one plane. This plane is defined in the drawings by the axis 83, and is perpendicular to the plane of the drawing.

FIG. 14 illustrates an arrangement wherein three test objects 90. 92, 92 are arranged so that their axes form the points of a triangle defined by the lines 93, 94, 95.

FIG. 15 illustrates an arrangement having two test objects 96, 97 which are not symmetrical.

What is claimed:

1. Testing apparatus for simulating the behavior of contact moving under normal force loading in machine components with at least two test objects including a second test object and at least one first test object which performs a rolling movement on the second test object, characterized in that at least the first test object (1, 1') during testing is driven by means of an eccentric arrangement, the latter comprising a first crank (10, 10') revolving at a substantially constant speed about a first spindle (5), as well as a second crank (11, 11'), which is articulated to the first crank (10, 10') on a second spindle (30) at a distance from the first spindle (5), together with a third crank (12, 12'), which is longer than the first and second cranks and is articulated to the second crank (11, 11') on a third spindle (31) at a distance from the second spindle and is provided with a spatially fixed spindle (2, 13) at a distance from said third spindle and the fixed spindle is connected in a non-rotary manner with spindles of the test objects.

2. Testing apparatus according to claim 1, characterized in that the inertia of the cranks (10, 10', 11, 11', 12, 12') is compensated for by counterweights.

3. Testing apparatus according to claim 1, characterized in that two test objects are provided, which are in each case driven by means of an eccentric arrangement.

4. Testing apparatus according to claim 1, characterized in that two test objects are provided, one of which is driven by means of an eccentric arrangement.

5. Testing apparatus according to claim 4, characterized in that two test objects are provided, which are driven by a common spindle.

6. Testing apparatus according to claim 1, characterized in that three test objects are provided, which are juxtaposed in such a way that their axes are in one plane.

7. Testing apparatus according to claim 1, characterized in that three test objects are provided, whose axes in section form the angle points of one of an equilateral and a scalene triangle.

8. Testing apparatus according to claim 1 characterized in that the test objects are rotationally symmetrical to their axis of rotation.

9. Testing apparatus according to claim 1, characterized in that the test objects are not rotationally symmetrical.

10. Testing apparatus according to claim 1, characterized in that the non-rotary connection is achieved by means of radial grooves, which are symmetrically arranged on the test objects.

11. Testing apparatus according to claim 1, characterized in that loading takes place hydraulically, pressure drop being brought about in a hydraulic loading device at movement reversal points.

12. Testing apparatus according to claim 1, characterized in that return travel takes place with reduced loading.

13. Testing apparatus according to claim 1, wherein the first test object perform a rolling movement with a superimposed sliding movement on the second test object.

14. Testing apparatus according to claim 1, characterized in that return travel takes place with no loading.

* * * * *